(12) United States Patent
Ketkar

(10) Patent No.: US 11,911,489 B2
(45) Date of Patent: Feb. 27, 2024

(54) SAPONIN-CONTAINING COMPOSITIONS FOR USE IN TEXTILE WIPES AND METHODS OF USE AND PREPARATION

(71) Applicant: Sanjeevita By Audubon, LLC, Norristown, PA (US)

(72) Inventor: Vaishali A. Ketkar, Norristown, PA (US)

(73) Assignee: Sanjeevita by Audubon, LLC, Audubon, PA (US)

(*) Notice: Subject to any disclaimer, the term of this patent is extended or adjusted under 35 U.S.C. 154(b) by 0 days.

(21) Appl. No.: 16/189,428

(22) Filed: Nov. 13, 2018

(65) Prior Publication Data

US 2019/0076338 A1  Mar. 14, 2019

Related U.S. Application Data

(63) Continuation of application No. PCT/US2017/032701, filed on May 17, 2017.

(60) Provisional application No. 62/336,245, filed on May 13, 2016.

(51) Int. Cl.

| | |
|---|---|
| *A61K 8/97* | (2017.01) |
| *A61K 8/02* | (2006.01) |
| *A61K 8/34* | (2006.01) |
| *A61K 8/73* | (2006.01) |
| *A61K 8/9728* | (2017.01) |
| *A61K 8/9789* | (2017.01) |
| *A61Q 15/00* | (2006.01) |
| *A61Q 19/10* | (2006.01) |

(52) U.S. Cl.
CPC ............ *A61K 8/0208* (2013.01); *A61K 8/345* (2013.01); *A61K 8/738* (2013.01); *A61K 8/9728* (2017.08); *A61K 8/9789* (2017.08); *A61Q 15/00* (2013.01); *A61Q 19/10* (2013.01); *A61K 2800/87* (2013.01)

(58) Field of Classification Search
CPC ...... A61K 8/0208; A61K 8/345; A61K 8/738; A61K 8/9728; A61K 8/9789; A61K 2800/87; A61Q 15/00; A61Q 19/10
See application file for complete search history.

(56) References Cited

U.S. PATENT DOCUMENTS

| | | | | |
|---|---|---|---|---|
| 2006/0003649 | A1* | 1/2006 | Runge | D04H 1/587 |
| | | | | 442/59 |
| 2007/0202062 | A1* | 8/2007 | Workman | A23L 29/04 |
| | | | | 424/66 |
| 2013/0295204 | A1* | 11/2013 | Silberstein | A61K 36/31 |
| | | | | 424/725 |

FOREIGN PATENT DOCUMENTS

CN          104814895 A  *  8/2015

OTHER PUBLICATIONS

Upadhyay, A.; Singh, D.K. Pharmacological effects of Sapindus mukorossi. Rev. Inst. Med. Trop. Sao Paulo, 54(5); 273-280. (Year: 2012).*
English translation of CN104814895-A retrieved from Espacenet on Mar. 21, 2022.*

* cited by examiner

*Primary Examiner* — Jessica Worsham
(74) *Attorney, Agent, or Firm* — Calderone Bullock LLC

(57) ABSTRACT

The invention includes saponin-containing compositions, wipes impregnated with these compositions, and related methods. Specifically, the invention includes a cleansing and deodorizing composition that includes a saponin; a deodorizer; cyclodextrin and a solvent. The saponin may be derived from botanical sources, such as, for example, *Sapindus mukorossi* or *trifoliatus*. Also included are textiles that are impregnated with the composition of the invention. Such textiles may be, for example, made of biodegradable materials. The invention also includes related methods of use and treatment.

31 Claims, No Drawings

SAPONIN-CONTAINING COMPOSITIONS FOR USE IN TEXTILE WIPES AND METHODS OF USE AND PREPARATION

CROSS REFERENCE TO RELATED APPLICATIONS

This application claims priority to International Application No. PCT/US2017/032701, filed May 15, 2017, which in turns claims priority to and the benefit under 35 U.S.C. § 119(e) to U.S. Provisional Patent Application Ser. No. 62/336,245, filed May 13, 2016, the entire contents of each of which are incorporated herein by reference.

BACKGROUND OF THE INVENTION

The consumer wipes market has seen significant global growth over the last decade. However, growing consumer concerns regarding chemical exposure and the evidence of environmental hazards posed by the discarded non-biodegradable wipes and residual chemicals within could have a negative impact on the future growth in the market. The growth potential of these products in well-established as well as emerging markets will therefore depend on the introduction of safer and more environmentally friendly products. Product development of less toxic and eco-friendly products is underway in response to the availability of toxicological data and reported incidents of chemical sensitivities, allergies, dry skin, contact dermatitis etc. from direct and indirect repeated contact with wipes and the cleaning compositions they contain. Apart from the toxic chemical residues that contaminate the soil and water post use, the non-biodegradable waste generated from such products also presents a negative environmental impact post use. To sustain the projected market growth specially, in the emerging world markets; innovative, safer, effective, biodegradable products made from renewable sources need to be developed.

Further, products made with application-specific high value features will drive further growth and innovation in this product segment. An increase in hygiene awareness and disposable income has contributed to the growth of wipe products in global markets. Wipe products that address consumer needs resulting from lack of basic resources will specifically help consumers in the emerging markets. Therefore, there is a need for product development that takes into consideration unique needs faced by consumers representing the developed as well as emerging markets.

The market lacks unique and distinct products developed with a holistic approach to deliver consumer friendly and ecofriendly products. Responding to chemical safety and environmental pollution concerns, there is a shift towards development of less toxic and biodegradable cleansing products and wipes. These types of products incorporate naturally derived biodegradable ingredients made from renewable sources e.g. naturally derived surfactants to replace petroleum based and synthetic surfactants. However, even though the new products contain eco-friendly naturally derived ingredients, chemically the materials used in the new products are either the same or similar to the materials used in conventional products. Therefore, though raw materials could be made using renewable sources in a more ecofriendly manufacturing process, the raw materials and the personal care products could still expose consumers to the same risks. Thus, most of these new products do not address the original consumer safety concerns even though the product labels may carry new verbiage like; natural, eco-friendly, green. etc.

Baby, facial, and body wipes constitute a large section of the overall cleansing and moisturizing wet wipes market that has seen a growth in niche wipe brands. Baby wipes are used to cleanse skin that could be especially sensitive owing to the direct exposure and contact with urine and fecal matter. Facial skin could be sensitive to pH, salt concentration, preservatives, fragrances etc. Chemicals from wet wipes used in conjunction with toilet tissue could sensitize skin when used by people who suffer from piles. Each set of cleansing application can thus carry unique considerations and may require specific product attributes that address the unique needs.

However, most cleansing liquids and wet wipes in widespread use are generally composed of synthetic or naturally derived fatty acid surfactants, fatty acid soaps, detergents, solvents, emollients, moisturizers, acidifying, alkalizing, oxidizing agents, salts etc. Some of these compounds and trace impurities present within contribute to toxic side effects. Cleansing products also contain concentrated synthetic fragrances or essential oils to mask malodors in order to provide a clean feel. Most formulations include moisturizers but the cleansing ingredients strip the skin of natural emollients leading to dry skin and some cleansers and fragrance compounds are known to trigger allergic response.

Further, the formulations also contain a number of additional synthetic chemicals; to extend shelf and in-use product stability, control bioburden, control physical-chemical stability to protect against changes in color, odor etc. With the widespread use of wipes for personal care, domestic and industrial use, more people come in direct contact with a varied class of synthetic chemicals, many of which have been identified as carcinogens, allergens, and sensitizers. Few niche formulations and wipes containing minimal ingredients are available for baby care, but most still do employ the use of synthetic chemicals and naturally derived surfactants. A handful of wet wipe products primarily contain only water thus, have limited cleansing efficacy. Hence, there is a need for development of effective and safer cleansing products for use in the wipes.

Most marketed deodorizing cleansing formulations and wet wipes primarily contain fragrant compounds to mask the malodors. The primary mechanism of deodorization is odor masking by means of using; fragrant compounds (e.g., essential oils), ingredients that entrap (e.g., cyclodextrin) the malodors or both. Antiperspirant and body deodorants specifically designed to counter the body and sweat malodor are observed to also incorporate germicides to control the microbes that breakdown sweat into compounds, which produce the malodor. Fragrant and odor entrapping compounds have also been incorporated in air fresheners and cleansers but these are observed to show limited efficacy. Some products employ application specific synthetic deodorizing compounds to neutralize specific malodors, e.g., odors from sulfur based compounds. All these options show limited deodorization efficacy and limited scope of application. Universally effective malodor removing products are not yet available as such agents would need wide range of neutralization potential against a number of specific chemical functional groups that are responsible for producing specific malodors. Blend of naturally derived enzymes employed in formulations disclosed herein thus presents a better solution for odor neutralization as these enzymes interact and neutralize the malodor emanated by a varied set of chemicals. Use of these enzymes in commercial products is primarily limited to sweat deodorization and feminine hygiene. A range of deodorizing products that effectively utilize the wide range of odor neutralization potential of the enzyme blend could be developed to provide better solutions to satisfy consumer needs. Products specifically useful for cleansing and deodorizing hands post food consumption are not available for personal use. Deodorizing products used in public restrooms mostly employ synthetic fragrances, air fresheners, antimicrobials, etc., only to mask the odors and expose people to toxic chemicals. Overall, the market lacks better natural deodorizing products for personal use, domestic sanitation, public sanitation for specifically eliminating wide range of malodors; body, food, vomit, urine, fecal matter, pets, etc.

Factors such as; non-woven fibers suitable for microbial growth, water based formulations, and room temperature storage make the wet wipes susceptible to bioburden growth therefore, wet wipes specifically, multi-use packs need preservation but most single use sterile wipes also contain preservatives. Though some preservatives are biodegradable, almost all preservatives in widespread use are synthetically derived. Increasing awareness about toxic side effects of most commonly used preservatives has led to the development of new products that contain preservative embedded non-woven webs, safer preservative blends, self-preserving systems, etc., to reduce exposure of consumers to preservatives. However, controls on materials, packaging, and manufacturing processes to control the initial bioburden have not been widely proposed or adopted. In addition to the toxic side effects, repeated exposure to some non-specific broad spectrum preservatives incorporated in topical skin care and cleansing products can affect the viability of skin's natural microbiota. The critical role the microbiota play in maintaining skin health and immune system is now being understood in greater detail. Therefore, to maintain natural microflora and to reduce chemical exposure, safer natural alternatives are being used in topical products and wet wipes. However, there is controversy around the undisclosed contents and composition of certain plant extracts used in these products as natural preservatives. Development of better alternative products is therefore needed to deliver consumer friendly and preservative free formulations and wipes.

Non-woven matrix made from synthetic fibers, regenerated cellulose fibers, and plant based fibers constitute the dry and wet wipe products used for personal, household, and industrial cleaning applications. The non-biodegradable synthetic fiber non-wovens account for majority of the wet wipes matrix and once used, the discarded wipes end up as solid waste in landfills where the non-biodegradable mass is estimated to sit for centuries. Due to the availability of flushable wet wipes, a significant section of the consumers use wet wipes in toilets in addition to dry toilet tissue. Unlike baby wipes that get discarded as solid waste along with soiled diapers, wet wipes used by adults in place of toilet tissue get flushed down the toilets. The flushability claim of wipes has been under close scrutiny as, upon disintegration the synthetic fibers used to make these wipes do not biodegrade. Many consumers do not read the fine print regarding the flushability claim as most products state to flush only 1-2 wipes at a time and could need more than 1.5 gallons of water per flush. As a result, in spite of the improved disintegration properties, most flushed wipes end up blocking the sewer systems and many end up contaminating the oceans and beaches. This impact of non-biodegradable wipes on water, environment, landfill, etc., has been reported globally.

Therefore, in order to deliver consumer friendly and ecofriendly products it is critical to effectively address the functional features as well as biodegradation aspect of the wipe matrix. Most biodegradable non-woven wipes are made of cotton and regenerated cellulose fibers. Due to the chemical processing, biodegradable wipes made from regenerated cellulose do not qualify for organic certification. Cotton farming needs significant water and material costs can be higher. Therefore, alternate biodegradable matrix options that possess good water absorption capacity, adequate wet strength and disintegration qualities need to be developed. Also, to address the varied public sanitation issues in the developing world, eco-friendly wipes developed specifically for use in compostable toilets need to be developed. The products disclosed in the current application offer alternate options to the marketed products to overcome these challenges.

BRIEF SUMMARY OF THE INVENTION

As described herein, the invention includes cleansing and deodorizing compositions that include a saponin; deodorizer; cyclodextrin, and a solvent. The saponin is selected from a dammarane, tirucallane, lupine, hopane, oleanane, taraxasterane, ursane, cycloartane, lanostane, cucurbitane, steroid and mixtures thereof.

Also included within the scope of the invention are textiles impregnated with this composition and methods of preparing the same by impregnating a textile with the composition of the invention. The invention further includes methods or leaning or deodorizing a surface, methods of removing a pollutant from or improving pollutant-mediated damage to a surface, methods of reducing the frequency of the occurrence of acne on a skin surface comprising wiping the skin surface, methods of repelling insects or arachnids from a surface that includes wiping the surface with such textiles.

Methods of cleaning or deodorizing a surface, of removing a pollutant from or improving pollutant-mediated damage to a surface, of reducing the frequency of the occurrence of acne on a skin surface, of reducing the frequency of the occurrence of insect and/or arachnid bites received on an area of skin, of ameliorating solar urticaria on a skin area, of ameliorating and/or preventing an occurrence of diaper rash on a skin area, of ameliorating and/or preventing an occurrence of a bed sore on a skin area, of promoting the healing of a wound including applying to the skin area an effective amount of the composition of the invention at least once a day are also included.

Methods of preserving a material comprising incorporating into the material the composition of the invention, wherein the composition is preserved from a substantial increase in a bacterial or a yeast/mold population over time are included.

DETAILED DESCRIPTION OF THE INVENTION

The present invention seeks to address and overcome the aforementioned disadvantages and deficiencies of the currently marketed cleansing products and associated textile wipes. The major objective is to provide consumers natural, hypoallergenic, and environment friendly product alternatives over the conventional synthetic products used for maintaining personal, domestic, and public hygiene and to prevent or ameliorate various skin conditions or disorders.

The invention includes saponin-containing compositions for various applications, including cleansing, deodorizing and/or moisturizing, as well as wipes that are impregnated with such compositions.

The ingredients of the composition of the invention may be wholly or partially natural. By "natural" it is meant that the ingredient or component comes from or is made from a renewable resource found in nature (flora, fauna, mineral), with absolutely no petroleum compounds. Such sources can include plant sources or botanical sources. As used herein, theses terms include materials developed from cultivated or wild plants, or obtained from wild, agriculturally or biotechnologically derived plant materials, for example, derived or obtained from plant cell lines or cell lines transformed or transfected with plant DNA or RNA, including plasmids or other vectors containing portions of plant DNA or RNA.

The benefits of the compositions and wipes disclosed could be well appreciated by the consumers. Described below are a few specific examples regarding the product applications, where the products can serve a specific consumer need or provide a solution to overcome lack of resources that limit the consumer's options to maintain hygiene:

Food is consumed by hand by a wide section of the population in countries like India. The food is cooked with a variety of different oils with characteristic odors; mustard, coconut, etc., using garlic, ginger, and a variety of fragrant spices. Upon consumption, effective hand washing is critical not only to remove food residues but also to effectively remove the oily residues and strong aromas. However, access to clean facilities equipped with clean water supply is not guaranteed. Cleaning with traditional fatty acid soaps, even when available is not very effective to remove oil and aromas specially, in the presence of hard water. Upscale restaurants typically provide warm water finger bowls to each customer with slices of lemons for hand cleansing but this method is also not very effective and is not adopted universally as it needs many resources. Thus, there is a need of providing effective cleansing agents that are milder for skin contact and are able to remove food and oily residues as well as odors. The liquid formulations and wipes disclosed herein provide an effective affordable solution to address this need at home and on the go, respectively.

The disclosed wet wipes provide a safe option for cleansing and deodorization as the saponins can effectively emulsify and remove the oily residues and the enzyme blend is effective in neutralizing spicy food odors. In the absence of availability of water for effective hand washing, the solution along with dry or wet wipes is an effective cleansing option that contains plant based biodegradable formulation.

A growing number of parents and teachers in developed countries rely on using liquid or gel hand sanitizers instead of using traditionally effective method of hand cleansing with water. The hand sanitizing liquids and gels are not effective in cleaning hands off any material residues. Most hand sanitizers contain non-aqueous solvents, synthetic fragrances, and broad spectrum antimicrobial actives that kill pathogenic as well as native skin microbes. Long term repeated use of such cleansers could have negative impact on health. Therefore, formulations and wipes disclosed herein are safe and very well suited for use on the go and in classrooms as these provide safer and effective cleansing and deodorization without leaving behind residues of toxic chemicals.

The disclosed formulations and wipes are effective in neutralizing odors from sweat, urine, fecal matter, vomit, etc., Thus, applicable uses include: baby wipes for diaper change, clean-up of diaper changing pad and changing stations in public spaces, adult incontinence wipes, clean up post vomiting, feet cleansing, etc.

Deodorization of pet bedding, pet care and adoption facilities, e.g., it is difficult to deodorize facilities that house multiple pets by simply using a litter box or by using standard cleansing and sanitizing agents.

When faced with natural disasters like floods, earthquake, etc., most people have little option than to take shelter in makeshift public disaster relief facilities. In some cases, people have to use such facilities for extended periods of time. In the absence of supporting infrastructure it is challenging for people to continue with personal daily rituals. People living in draught affected areas face similar problems due to limited access to water. The biodegradable natural wet wipes thus provide an effective solution to maintain hygiene while reducing the amount of water used for personal cleansing while keeping the post use environmental impact to a minimum compared to other marketed products.

Over the years private companies and non-profit organizations have developed different compostable toilet designs for private and public use. Many national parks use compostable toilets and in similar manner these could be adopted for use in developing countries to save infrastructure resources. Some companies and non-profit organizations have undertaken development of new designs and their field trials. Dry composting toilets have been designed for use at facilities not fitted with utilities. Water accounts for more than 90% content in such toilets, which needs to be separated for effective aerobic composting.

The biodegradable natural fiber wet wipes disclosed herein thus present a viable solution for use with such compostable toilets as they limit the use of water by the user and get composted without leaving behind chemical residues. Also, the natural fiber wipes are able to retain moisture and have good water absorption capacity, which assists the aerobic decomposition process. Whether one has to use such facilities in remote national parks or in an earthquake-affected zone, the disclosed product effectively and safely addresses the consumer needs and has low post use environmental impact as it uses natural, renewable, biodegradable ingredients.

Most developing countries lack adequate infrastructure even within urban areas to process sanitary waste, which leads to chemical contamination of soil and water from everyday use marketed cleansing products. The unique blend of the saponins and the odor neutralizing enzymes in the disclosed products provides an added advantage of eliminating malodors from public facilities that are chronically plagued with the malodors due to the lack of availability of cleansing solutions and adequate water supply for cleansing. In many countries, malodor from public use facilities is one of the major deterrents that prevents most people from using them. Thus, the disclosed products and their varied delivery forms such as; liquid formulations, wipes, controlled release gels, floating tablets, etc., can provide an effective option for cleansing as well as deodorization of specific malodors from such places without leaving behind harmful residues that would contaminate the environment.

Major segments of the population in developing countries still lack basic resources like direct residential supply of clean water, dry toilet tissue, etc., to help maintain personal hygiene. Lack of soap and water supply further compound the unsanitary and unhygienic conditions that can promote spread of infections and diseases. Water, when available usually is manually hauled in buckets to the facility by individuals. The disclosed liquid formulations and wet wipes thus provide effective cleansing option to rural as well as urban populations that lack adequate resources. The adoption of easy to use biodegradable cleansing and deodorizing product like the disclosed wet wipes can help improve hygiene and sanitation in spite of the chronic lack of water supply. Use of a bidet and water spray is prevalent in some European countries and most of the countries in South East Asia for personal cleansing over the use of dry toilet tissues. However, availability of such facilities is mostly restricted only to private residences. Therefore, with increasingly dynamic lifestyle of people specifically, in developing countries in South East Asia the flushable biodegradable wet wipes disclosed herein can provide an effective personal cleansing alternative when facilities like bidet or water spray are not available. The disclosed products provide a better solution to the consumers over the marketed products; dry wipes and tissues that lack the wet strength, the standard marketed wet wipes that contain chemicals and contribute to non-biodegradable environmental waste.

The use of flushable wet wipes is growing in developed countries yet there are no specific solutions that have chosen to address the biodegradable and hypoallergenic content of the liquid formulation and compostable content of the wipe matrix.

The hypoallergenic, soothing and healing properties of the formulation may be specifically critical for cleansing applications related to diaper rash, bedsores, hemorrhoids, etc. The wash off and leave in formulations are useful owing to the multifunctional properties and select grades of ingredients.

Saponins, cyclodextrins, shikimic acid, aloe etc. may be critical to support these applications that make use of their physico-chemical properties and pharmacological actions, e.g., surface activity of saponins that helps in cleansing also provides solubilization of compounds like cholesterol for delivery to skin (e.g. foot care) and can also act as anti-oxidants to prevent damage and promote healing, cyclodextrin can increase solubility by complexation and can also act as controlled delivery of anti-oxidants or solubilization of enzymes/proteins contained in body fluids that could be otherwise difficult to clean and remove with some surfactants.

As discussed in more detail below, the compositions and textiles of the invention contain both saponin and cyclodextrin. Such combination is particularly useful in the personal care arena, for example, for cleansing or treating hair, skin or nails. In addition, such compositions are hypoallergenic and facilitate hair/skin/nail remediation after exposure to pollutant chemicals in the air and/or water. Applications of these compositions may also be extended to care of hard surfaces in residential, institutional and commercial applications.

The invention includes a composition containing one or more saponins, preferably a naturally occurring saponin. Naturally occurring saponins have been used the world over for cleansing applications for centuries owing to their surface activity and emulsification properties. Saponins from Quillaja and Yucca have been widely used for varied industrial applications and to formulate organic toothpaste. The surface active saponins are mild on skin and have been demonstrated to exhibit effective skin and hair cleansing properties as noted in their traditional use over the centuries as well as their use in patented products and applications.

Saponins are amphiphilic surface active secondary metabolites synthesized by plants. The chemical makeup of saponins lends surface activity to these compounds as they contain hydrophilic glycosides (glycone) and lipophilic non-sugar (aglycone) triterpenoid or steroid portion within a molecule. Saponins are present in wide variety of plants and vegetables like quillaja, yucca, soybean, soap nut, etc., Saponins are also present in marine animals. Prior to wide spread use of fatty acid soaps, saponins were used for various cleansing applications.

Some saponins exhibit chemical and pharmacological properties of alkaloid natural products as the aglycone derivatives can contain nitrogen. Because of the unusual chemical structures of saponins, they exhibit multifunctional properties, including, for example, cleansing, disinfectant/antibacterial, antifungal, insect repelling, insecticidal, spermicidal, arachnid repellant or cidal (e.g., ticks and mites), surfactant, etc. Accordingly, the compositions and impregnated textiles described herein can be used to treat/address any conditions for which the saponin(s) have functionality, e.g., to formulate cleansing and soothing skin care products for acne and impetigo, after exposure sun or pollution, mild cleansing without irritation, etc.

*Sapindus Mukorossi* and/or *Sapindus trifoliatus* nut extracts have been extensively used in Indian households for cleaning hair, jewelry, silk, and/or wool. The present composition uses saponins that are preferably extracted from nuts of *Sapindus Mukorossi* and/or *trifoliatus*. However, saponins derived from any botanical source may be suitable, including plants of the Family Sapindaceae and plants of the genus *Sapindus*. Any mixture or blend of saponins may be used, including, without limitation, saponins from the subtypes dammarane, tirucallane, lupine, hopane, oleanane, taraxasterane, ursane, cycloartane, lanostane, cucurbitane, steroids and mixtures thereof.

The saponin(s) may be present in the composition in any amount. It may be preferred that they are present in an amount of about 0.01% to about 70% by weight of the total composition. Alternatively, the saponin(s) may be present in an amount of about 1% to about 60%, about 5% to about 50%, about 10% to about 40%, and/or about 20% to about 30% all by weight of the total composition.

Cyclodextrin is also included in the composition. Any type or a mixture of types may be included, for example, uncomplexed parent cyclodextrins α, β, γ or their derivatives, e.g., hydroxypropyl-beta-cyclodextrin, hydroxyl-propyl-gamma-cyclodextrin. Complexed cyclodextrins may also be used, such as those that are complexed with anti-oxidants. Selection of complexed versus uncomplexed (or a combination of both) may vary depending on the end formulation and/or end use.

The cyclodextrin(s) may be present in the composition in any amount. It may be preferred that they are present in an amount of about 0.01% to about 10% by weight of the total composition. Alternatively, it may be present in an amount of about 1% to about 9%, about 2% to about 8%, about 4% to about 7%, and/or about 5% to about 6%, all by weight of the total composition.

The composition may have any pH, depending on the ingredients it contains and/or the end use. However, it may be desired that the composition has a pH in a range of about 2 to about 7. In an embodiment that may be preferred, such pH can be achieved without the addition of additional acidic ingredients to the composition solely for the purpose of adjusting the pH. For example, citric and ascorbic acids included in the composition for their anti-oxidant properties will also serve to lower the pH of the overall composition. "About" as used in this context has the meaning of "approximately", for example, plus or minus 0.5 unit of pH.

Citric acid and ascorbic acid added as anti-oxidants will provide acidic pH BUT the main formulation ingredients (by themselves) like saponin extract, enzyme deodorizer, shikimic acid, aloe etc. all contribute to acidic pH without the need for pH adjustment in acid range.

The composition may also have in it one or more deodorizers. Such deodorizers are preferably derived from plants or other natural sources; any known or to be developed may be used. Suitable enzyme deodorizers may include, without limitation, plant-extracted hydrolases, deesterases, reductases, oxidases and blends thereof. Suitable blend may include those disclosed within United States Patent Application Publication Nos. 2014-0066869 A1 and 2005-0186255 A1, the contents of each of which are incorporated herein by reference. Other added compounds may include deodorizing zinc ricinoleate and multifunctional shikimic acid which may function, in some compositions, as deodorizer The deodorizer(s) may be present in the composition in any amount. It may be preferred that they are present in an amount of about 0.1% to about 25% by weight of the total composition. Alternatively, it may be present in an amount of about 1% to about 20%, about 5% to about 15%, and/or about 10% to about 17%, all by weight of the total composition.

Shikimic acid may be included as a deodorizer but is a multifunctional ingredient, so may confer to the compositions additional functionalities, e.g., inhibition of lipase activity to control sebum (to aid in control of acne), to control body odor by blocking enzymatic pathways, exfoliation of skin and antimicrobial, so helpful in skin and scalp treatment. When used not for its deodorant effect, the amount of shikimic acid may be lesser, depending on the end formulation and/or end use.

In some embodiments, the composition also includes a surfactant or co surfactant; preferably, it is a natural surfactant. Exemplary materials may include lecithin, pea protein, soy protein isolate, soy protein hydrolysate, alkyl polyglycosides, amino acid based-surfactants, glycolipid biosurfactants, and alkyl glucosides.

In various embodiments of the composition, a surfactant or co-surfactants may be present in the composition. In some embodiments, it may be present in an amount of about 0.5% to about 15%, about 1% to about 10%, about 5% to about 7%, all by weight of the total composition.

In some embodiments, the composition may include a solvent, preferably an aqueous or water miscible solvent, such as a water miscible humectant solvent. Any known or to be developed may be used, so long as it is suitable for use on the surface to which the composition is to be applied (e.g., safe for use on skin, safe for use on stainless steel). Suitable solvents may include aqueous based solvents, water, water-miscible humectant solvents, hydrosol, and plant or flower waters, such as cherry water, lemon water, kiwi water and the like. Glycerin may also be used as a solvent.

Hydrosols include, for example, suitable hydrosols could include hydrosols of neem, calendula, witch hazel, chamomile, *Echinacea*, vetiver, tea tree, eucalyptus, lavender, *Rosmarinus officinalis*, rose geranium, oregano, summer savory, anise, cumin, balsam fir, cedarwood, black thyme, *Boswellia carterii*, neroli, *Mentha piperita* and mixtures of the same.

In various embodiments, the solvent may be present in the composition in any amount. It may be preferred that they are present in an amount of about 0.5% to about 10% by weight of the total composition. Alternatively, it may be present in an amount of about 1% to about 7%, about 2% to about 5%, and/or about 3% or 4%, all by weight of the total composition. In some embodiments, solvent could also be formulation vehicle that could be used as quantity sufficient (q.s.) to about 100%.

As used herein, the term "about" has the meaning of "approximately" or, for example, plus or minus 5% of the stated amount.

Other additives and ingredients as desired may be added to the composition. For example, if the composition is to be applied to skin, hair or nails, one may consider including aloe vera, in any form, such as for example, an extract or a gel, to provide, for example, additional skin moisturization, anti-inflammatory and antimicrobial properties. As used herein, the term "aloe vera", unless specified, includes all forms of the plant described herein, such as raw, processed, extracts, gels, powders, and those described below, and can include components from the inner filet and/or the whole leaf. It may be preferred that the aloe vera gel used is prepared using a cold process to ensure maintenance of the natural properties of the aloe vera.

Native and modified material grades of whole leaf and inner leaf aloe vera gel could include; stabilized gel, powder for reconstitution (e.g., lyophilized, solar dried, spray dried, dehydrated leaf etc.), aloe vera gel concentrate, etc. In addition to cleaning and moisturization, use of formulated liquids and wet wipes for applications such as; restoration of immune function, wound repair/healing of sensitized skin (e.g., sun exposure, injury, burn/scald, diaper rash, bed sores, hemorrhoids, etc.) grades of aloe vera gel, which are specifically high in the concentration of acemannan compared to conventional aloe vera gel are recommended. For better product efficacy, use of selective molecular weight grades of the aloe polysaccharides is recommended.

In some embodiments, particularly specialized applications, the preferred aloe vera gel or extract may be of a specific molecular weight, depending on the end use applications. For example, grades of aloe vera powder and gel are available with select molecular weight distribution. Typical native aloe vera gel contains >2000 kDa molecular weight polysaccharides. Enzymatically processed fractions of the aloe gel in the range of 50 to 400 kDa range may be useful if the end application is related to skin care, especially skin care post-sun and/or wound healing. In other or similar embodiments, it may be preferred to use an aloe vera gel or extract that has been modified to contain selected levels of acemannan, for example of about 5% to 30% or more and/or with molecular weights in a range of 50-200 kDa.

Overall, it may be preferred to include the selected aloe vera in amounts of about 0.1% to about 50% by weight of the total composition.

In addition, other additives may be included, such as conventional preservatives, glycerin, UV filters, additional surfactants, fragrances, colorants, petrolatum, waxes, zinc oxide, pigments, whiteners, opacifiers, sensates buffering agents, alcohols, extracts of *Saccharomyces*, metal chelaters, acid/base/buffers, stabilizers, anti-oxidants, botanical, herbal and mineral extracts, oils, or ingredients (such as turmeric, ginger, seaweed, red and brown algae, sandalwood, mint, grapefruit, comfrey, apple, sage, lavender, cinnamon, iris root, cotton thistle, saffron, cucumber, papaya, pineapple, lotus water, cherry water, kiwi water, lemon water, chia, henna leaves, camphor, psyllium husk, rice, lemongrass, citronella, lemon eucalyptus, eucalyptus, capsicum, oatmeal, zinc, copper, and manganese), neem, and menthol.

In an embodiment, the composition contains glycerin in an amount of about 0.5% to about 10% by weight. Alternatively, it may be present in an amount of about 1% to about 7%, about 2% to about 5%, and/or about 3% or 4%, all by weight of the total composition.

The composition may be developed into any format, such as a liquid, solid, semi-solid, gel, paste, and suspension. It may be contained in capsules, such as gelatin, acrylic polymer or other polymer beads (which may, if desired, be formulated for controlled release). In an embodiment, such beads or capsules are included within another carrier, e.g., such as acrylic beads suspended in a gel.

In some embodiments pharmaceuticals may be included, such as, for example, those used in the topical treatment of disorders of the skin, hair or nails. For example, one may include pharmaceutically active saponins, salicylic acid, anti-acne compounds, anti-impetigo compounds, anti-hemorrhoid compounds, anti-fungal compounds, antibiotics, hydrocortisone, insecticides, shikimic acid, benzyl alcohol, compounds to promote wound cleansing and healing, allantoin, emollients such as squalene, squalane, lauryl laurate, isoamyl laurate, caprylic capric triglyceride, local anesthetics, astringent, vegetable ferments, *Saccharomyces* ferment, etc.

In some embodiments, the composition is formulated so as to be substantially conventional "preservative free", that is to exhibit requisite shelf stability in the absence of conventional preservative chemicals, such as parabens. In some embodiments, the components of the inventive composition (e.g., saponin extract, aloe gel and *Saccharomyces* ferment) described herein may, when combined is sufficiently acidic that the composition, be self-preserving—i.e., no added acid would be needed to acidify the composition to a level to retard microbial growth. Alternatively, preservation may be accomplished by any means known or to be developed in the art. For example, the composition may be prepared with an acidic pH to limit the growth of pathogenic microbes. In another, the composition may be prepared to contain polyols that reduce or depress the rate of microbial growth; this is one approach that is widely employed as it also helps to maintain native skin pH. Other approaches are described in, for example, U.S. Pat. Nos. 4,772,501; 5,049,440; and 4,781,974, the contents of each of which are incorporated herein by reference. In an embodiment, the composition (and the textiles and/or containers of the invention described below) may be manufactured via aseptic processes in sterile product manufacturing facilities as is known in the art.

In addition to formulation's self-preserving capacity, preservatives may be selected based on their efficacy, end use, product form (liquid formulation vs. wet wipe), and product pH range. Preservatives selected will depend on the adsorption profile of the wipe matrix and/or the regulatory status of the preservative in the product market.

In some embodiments, it may be preferred that the product has a pH of about 2 to about 7, 8, or 9.

The invention also includes a textile that is impregnated with any of the compositions described above. In such embodiment, the invention can take the form of pre-moistened and/or pre-medicated "wipes" for hair, skin, nails and/or other surfaces such as counters, tables, walls, dishes, etc.

The textile may be any known or to be developed in the art. In some embodiments, it is preferred that the textile is biodegradable, naturally-derived, produced by sustainable and/or 'green methods', and/or flushable. The textile may be of a matrix that is woven, non-woven, or a combination of the same. One-ply or two-ply may be preferred for wipes.

The textile may include a synthetic or a natural fiber, or a combination or hybrid of the same. Suitable textile materials may include rayon, acetate, polyester, aramid, acrylic, ingeo, olefin, regenerated cellulose, polylactid, bamboo, lotus stem, cotton, banana pseudo stem, pineapple leaves and/or stem, deciduous wood, palm, abaca, coir, jute, flax, kapok, kenaf, hemp, modal, ramie, sisal, soy protein and combinations thereof.

In one embodiment, the wet wipes are made using biodegradable matrix made of cotton fibers. In another embodiment, the wipe matrix could be made up of manmade fibers (ingeo, regenerated cellulose; Viscose, Lyocell) or their blend with natural and synthetic fibers. In a refinement, the biodegradable wipes are made of natural fibers like lotus stem and those sourced from agricultural waste like banana pseudo stem and pineapple leaves/stem that possess better water absorption and strength than commonly used fibers like cotton and regenerated cellulose.

In a refinement, the wipes are made using regenerated cellulose fibers, which are made using an environmentally friendly process, e.g., Lyocell process, over the viscose process. In a further refinement, the natural fibers used for making the non-woven matrix are processed mechanically to reduce the environmental impact of waste generated through chemical processing, e.g., banana fiber generated through mechanical processing yield better water absorption capacity as is known in the art.

In an embodiment, the wipes are made exclusively of banana fiber for fire related cleanup efforts due to the fiber's fireproof qualities. In another embodiment, the wipes are made using banana fibers that show good water and oil absorption properties so that the wipe matrix will also contribute to the cleansing efficacy in addition to the formulation constituents like saponins and cyclodextrin for the cleansing of water miscible and oily residues, e.g., cleansing of hands off food residues. In yet another embodiment, the wipe matrix could be made up of conventional synthetic non-biodegradable fibers and their blend with natural and naturally derived fibers.

In one embodiment, mechanically processed lotus stem fibers are used to prepare the woven matrix similar to wipes prepared using bamboo fibers. The soft cloth is used in conjunction with the cleansing and deodorizing formulations and suitable for application as reusable wipes.

The specific textile may be selected depending on the end use applications and certifications desired. For example, although plant based and biodegradable, the regenerated cellulose fibers do not qualify for organic certification. In some embodiments, natural fiber matrix processed to medical grade standards are used for specific product applications like wound cleansing.

The textile may be of any dimension; such dimension will vary depending on the end use of the textile. A textile intended for an end use as a baby skin wipe, for example, will likely have a smaller dimension than a wipe that is for use in cleaning the outer surface of an automobile. In some embodiments, the textile may have a dimension that provides an aspect ratio of about 1:1.2, about 1:1.5, about 1:1.7, and about 1:2.

In an embodiment, the textile has a dimension selected from about 3 inches by about 5 inches, about 4 inches by about 6 inches, about 5 inches by about 7 inches, about 6 inches by about 8 inches, about 7 inches by about 9 inches, about 10 inches by about 13 inches, and about 12 inches by about 12 inches.

In the practice of the invention, the textile is impregnated with the composition, either during manufacture or by the end user. In some embodiments, the textile is fully saturated with the composition, or is saturated to a level of about 50%, about 60%, about 70%, about 75%, about 80%, about 85%, about 90%, about 95%, and about 100% of the saturation capacity of a matrix of the textile, where "saturation capacity" is the total amount of a liquid that the textile is able to absorb in one instance.

The textile or textile(s) may be packaged for consumer use using any package or dispenser known to be developed in the art. For example, conventional packing of bags, pods, or boxes may be used. Packaging may be sterile or non-sterile.

Ingredients for use in the composition of the invention may be procured or are processed prior to manufacture:

Saponins may be extracted from soap nut pericarp per established procedure or ready to use saponin extracts could be procured from vendors.

Aqueous and non-aqueous extracts of *Sapindus Mukorossi* supplied by vendor could be used (e.g., 70% ethanolic extract, 70% aqueous extract) could be used.

Saponin extracts from other plant sources could also be used dependent on product application.

Refined and purified saponin extracts with isolated constituents could be used for specific applications (e.g., therapeutic).

Dry powder for reconstitution or stabilized aloe vera gel in native or modified forms can be procured from vendor or aloe vera gel is extracted under cold processing prior to use per established procedures.

Native or derivatized grades of cyclodextrins and/or uncomplexed or complexed cyclodextrins may be procured from vendors and used for target product application.

Different stabilized grades of deodorizer are procured from vendors and used for the target product application.

Different grades of co-surfactants are procured from vendors and used for the target product application.

Also included within the scope of the invention are various methods of preventing, treating, ameliorating the effects of and/or removing several conditions, disorders and materials. Such methods include application of the composition (neat or in a wipe or with other applicator) to a surface. Such methods can include cleaning, deodorizing, a surface, reducing the occurrence of acne or infection on a skin or wound surface, facilitating wound healing, preventing flesh putrification, reducing the occurrence of insect and/or arachnid bites on an area of mammalian skin, repelling or reducing the population of insects and/or arachnids on a surface or in an enclosed space, such as a room, drawer, car, shoe/boot, luggage and the like. Also, included are methods of destroying spermatozoa, and methods for preventing or ameliorating diaper rash, solar urticaria, bed sore(s), and tissue necrosis.

The surface can include skin, hair or nails of a mammal, such as a human. The surface may also include any hard or soft surfaces found in industrial, commercial, and/or institutional contexts, such as, for example, surfaces of desks, counters, utensils, dishes, pens, books, beds, meal trays, bedpans, shelves, cards, telephones, computers, office supplies, medical devices or implements, walls, boats, elevator interiors, bedding, seating, railings, carts, vehicles, chairs, curtains or blinds, shades, registers, toilet, sinks, showers, floors. The surfaces may be of any materials: for examples, papers, card, Bristol board, wood, metal, fiberglass, marble, plastic, vinyl, cement, stone, polymer, linoleum, glass, ceramic, clay, and earthen.

Pollutants may be removed from any of these surfaces using the methods of the invention. Application of the composition (neat or in a wipe or with other applicator) may be useful to remove deposits of pollutants, particulate matter related to the pollutants, and/or to ameliorate any damage to the surface that exposure to the pollutant may have caused. Pollutants may include, for example, naphthalene, acenaphthylene, acenaphthene, fluorene, phenanthrene, anthracene, fluoranthene, pyrene, benz[a]anthracene, chrysene, benzo[b]fluoranthene, benzo[k]fluoranthene, benzo[a]pyrene, dibenz[a,h]anthracene, benzo[ghi]perylene, indeno [1,2,3-cd]pyrene, benzo[c]fluorine, cyclopenta [cd]pyrene, dibenzo [a,e]pyrene, dibenzo [a,h]pyrene, dibenzo [a,i]pyrene, dibenzo [a,l]pyrene, 5-methyl chrysene, ozone, nitrous oxide, and oxides of sulfur.

Reductions in the incidence, severity and/or frequency of various diseases, disorders and/or irritations of the skin may be accomplished by the practice of the methods of the invention. For example, application of the composition (with or without wipe or applicator) may be used for acne, diaper rash, bedsores, promotion of wound healing, solar urticaria, skin irritations from urine, conventional soaps/detergents, skin chafing, immune-mediated urticarias, insect bites and stings, hemorrhoids, burns, etc.

In such contexts, the methods include application of an effective amount of the composition to the relevant area of skin. By "effective amount", it is meant an amount that produces the therapeutic response or desired effect in a patient over a specified period of time, and will vary depending on several factors, such as the individual patient's state, the problem being treated, the desired end result, the number of applications, etc. In general, an effective dose may be between 0.1 to 10 mls per 3 cubic centimeters of skin area. Application may be 1, 2, 3, 4, 5, 6, or 10 or more times a day, if desired.

The frequency of the occurrence of insect and/or arachnid bites received on an area of skin may be reduced and or eliminated using the method of the inventions and applying to the area of skin the composition (neat or on wipe or other applicator). In some embodiments, the composition used in this method may include extracts of neem, lemon eucalyptus, and citronella.

Spermatozoa and the bacteria that cause venereal diseases may also be destroyed by contacting it with the composition of the invention. For example, the composition may be applied to surfaces of a birth control device before use or may be applied directly to skin, mucosal surfaces or the surfaces defining internal body cavities.

In an embodiment of the invention, a method of preserving a material comprising incorporating into the material the composition of the invention so that the material is preserved, that is, the material when sealed exhibits no substantial increase in a bacterial or a yeast/mold population over time. Such materials may be a food, a personal care composition, a cosmetic, a paint, and a home care composition.

Manufacture of the composition, the textiles, and the packaging may be carried out using processes that are known in the art. In some embodiments, aseptic processing or sterile processing may be preferred. Preferably, manufacturing processes that reflect 'green principles', zero waste, and/or zero or minimized footprint are employed.

EXAMPLES

Various compositions of the invention are prepared by mixing all the ingredients of Table 1 together at room temperature in the amount(s) set forth in Table 1.

TABLE 1

| Ingredient | Potential Function | wt % | Preferred wt % |
|---|---|---|---|
| Saponin Extract (single source or blend of saponins) | Multifunctional surface active agent | >0.01 < 70 (saponin content) | 0.1-20 (saponin content) |
| Vegetable stock ferment | Odor neutralizer | 0.1-25 | 0.5-10 |
| Aloe Vera Gel | Cleanser, moisturizer, soothing agent etc. | 0.1-50 | 1-15 |
| Thickening agent | Viscosity builder, controlled release agent | 0.1-20 | 0.1-2 |
| Hydrosols | Fragrance and other functions | 1-15 | 8-12 |
| Glycerin | Solubilizer, moisturizer | 1-10 | 2-5 |
| Emollients | Skin Feel and moisturization | 0.5-10 | 2-5 |
| Plant extracts | Multi-functional: anti-inflammatory, anti-oxidant, anti-microbial, tone, soothe, regenerate, moisturize etc. | 0.01-10 | 1-5 |
| Mineral extracts | | 0.01-10 | 1-5 |
| Co-surfactants | Emulsification | 0.5-5 | 1-2 |
| Cyclodextrins | Complexing agent to solubilize and entrap varied chemicals | 0.01-10 | 0.1-2 |
| Benzyl Alcohol | Antimicrobial Preservative | 0.1-2 | 0.5-1.0 |
| Antimicrobial preservatives and extracts | Antimicrobial Preservative | qs | qs |
| Acid/base/buffers | pH adjustment | qs | qs |
| Anti-oxidants | Stabilizer | qs | qs |
| EDTA salts | Stabilizer: metal chelator, preservative adjuvant | qs | qs |
| Essential oils | Fragrance | qs | qs |
| Hydrosols/Plant or flower water Deionized Water, 18.2 MΩ-cm Purified Water, USP Water for Injection, USP | Formulation vehicle | qs to 100% | qs to 100% |

The compositions can be used for various end uses, including treatment of conditions of the hair, skin and nails (such as sun or pollution exposure, acne, deodorization, etc.) and application to hard surfaces in residential or commercial environments (such as counters, rails, sanitary ware, doorknobs, etc.) to deodorize and disinfect.

Example 2

A fatty acid soap and synthetic detergent-free composition for use in a deodorizing cleanser, is prepared by mixing the ingredients of Table 2 together in the amount set forth in Table 2. The composition may also be impregnated into a textile to prepare a wipe for application.

TABLE 2

| Ingredients | Grade | % w/w |
|---|---|---|
| *Sapindus Mukorossi* Extract | 70 wt % Ethanolic Extract | 1 to 5 |
| *Saccharomyces* Ferment | Organic | 1 to 10 |
| Hydroxypropyl Beta Cyclodextrin | Cosmetic/Pharma | 0.5 to 1 |
| Glycerin | Organic | 2 to 5 |
| Benzyl Alcohol | NF | 0.5 to 1 |
| Ethanol | Organic | 0.1 to 1 |
| Water | Reverse Osmosis | q s to 100 |

Example 3

An oil-free composition for soothing skin treatment is prepared in accordance with the invention. The ingredients of Table 3 are mixed together in the amounts set forth in Table 3.

The composition may be applied by a pre-impregnated wet wipe if desired.

Example 3

| Ingredients | Grade | % w/w |
|---|---|---|
| *Sapindus Mukorossi* Extract | 70 wt % Aqueous Extract | 0.5 to 2 |
| *Aloe Vera* Gel | Modified Aloe, 10 to 30% acemannan | 15 to 30 |
| Glycerin | Organic | 2 to 5 |
| Cotton Thistle Extract | Aqueous Extract, Personal Care | 1 to 2 |
| Hydroxypropyl Beta Cyclodextrin | Cosmetic/Pharma | 0.5 to 1 |
| Shikimic acid | Personal Care | 0.5 to 1 |
| Benzyl Alcohol | NF | 0.4 to 1 |
| Turmeric Extract | Personal Care | q s to 100 |

Example 4

A synthetic detergent- and oil-free composition for cleansing and toning oily skin is prepared in accordance with the invention. The ingredients of Table 4 are mixed together in the amounts set forth in Table 4.

The composition may be applied by a pre-impregnated wet wipe if desired.

TABLE 4

| Ingredients | Grade | % w/w |
|---|---|---|
| Sapindus Mukorossi Extract | 70 wt % Aqueous Extract | 0.5 to 2.5 |
| Shikimic acid | Personal Care | 0.5 to 2 |
| Hydroxypropyl Beta Cyclodextrin | Cosmetic/Pharma | 0.5 to 2 |
| Aloe Vera Gel with Lemon Juice | Organic, cold processed | 5 to 15 |
| Glycerin | Organic | 2 to 5 |
| Benzyl Alcohol | NF | 0.5 to 1 |
| Saffron | Food Grade | 0.05 |
| Calendula Hydrosol | Organic | q s to 100 |

Example 5

A synthetic detergent free emollient composition for use to cleanse dry skin is prepared by mixing the aqueous and oily phase ingredients of Table 5 in the amount set forth in Table 5 followed by homogenization.

TABLE 5

| Ingredients | Grade | % w/w |
|---|---|---|
| Sapindus Mukorossi Extract | 70 wt % Aqueous Extract | 0.5 to 2.5 |
| Shikimic acid | Personal Care | 0.5 to 2 |
| Hydroxypropyl Beta Cyclodextrin | Cosmetic/Pharma | 0.5 to 2 |
| Aloe Vera Gel | Organic, cold processed, stabilized | 10 to 20 |
| Glycerin | Organic | 2 to 5 |
| Benzyl Alcohol | Personal Care | 0.3 to 0.5 |
| Sodium Benzoate | Personal Care | 0.1 to 0.3 |
| Potassium Sorbate | Personal Care | 0.05 to 0.15 |
| Lauryl Laurate | Non-GMO, Personal Care | 2 to 5 |
| Lecithin | Organic, Soy | 0.5 to 1 |
| Kiwi Water | Organic | q s to 100 |

Instead of lauryl laurate, naturally derived emollients, such as isoamyl laurate (plant derived) and/or caprylic capric triglyceride (plant derived) may be used.

Example 6

A synthetic detergent- and oil-free composition for use to cleanse facial make up is prepared by mixing ingredients of Table 6 in the amount set forth in Table 6.

TABLE 6

| Ingredients | Grade | % w/w |
|---|---|---|
| Sapindus Mukorossi Extract | 70 wt % Aqueous Extract | 2 to 5 |
| Shikimic acid | Personal Care | 0.5 to 1 |
| Hydroxypropyl Beta Cyclodextrin | Cosmetic/Pharma | 0.5 to 2 |
| Aloe Vera Gel | Organic, cold processed, stabilized | 10 to 20 |
| Glycerin | Organic | 2 to 5 |
| Benzyl Alcohol | Personal Care | 0.3 to 0.5 |
| Sodium Benzoate | Personal Care | 0.1 to 0.3 |
| Potassium Sorbate | Personal Care | 0.05 to 0.15 |
| Sandalwood Hydrosol | Personal Care | q s to 100 |

This formulation is also potentially useful for cleansing oil, proteins (e.g., tears), cigarette smoke, etc.

Example 7

A fatty acid soap/detergent free composition for use in a cleansing and deodorizing wet wipe is prepared by mixing ingredients of Table 7 in the amount set forth in Table 7. This wipe can be used when dining as a fingerbowl hand towel.

TABLE 7

| Ingredients | Grade | % w/w |
|---|---|---|
| Sapindus Mukorossi Extract | 70 wt % Aqueous Extract | 2 to 5 |
| Saccharomyces Ferment | Personal Care | 2 to 5 |
| Hydroxypropyl Beta Cyclodextrin | Cosmetic/Pharma | 0.5 to 2 |
| Aloe Vera Gel | Organic, cold processed, stabilized | 10 to 20 |
| Glycerin | Organic | 2 to 5 |
| Ethanol | Organic | 0.2 to 0.5 |
| Benzyl Alcohol | Personal Care | 0.3 to 0.5 |
| Sodium Benzoate | Personal Care | 0.1 to 0.3 |
| Potassium Sorbate | Personal Care | 0.05 to 0.15 |
| Rose Hydrosol | Personal Care | q s to 100 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A cleansing and deodorizing multifunctional composition comprising:
   a. a saponin in an amount of about 0.1% to about 20%;
   b. a deodorizer;
   c. an uncomplexed cyclodextrin in an amount of about 0.1% to about 10% to solubilize with the saponin, and
   d. a solvent, wherein the saponin is selected from a dammarane, tirucallane, lupine, hopane, oleanane, taraxasterane, ursane, cycloartane, lanostane, cucurbitane, steroids and mixtures thereof and, upon application of the composition to a surface of hair, skin or nails, the surface is cleansed and deodorized without destruction of native microbes.

2. The composition according to claim 1, wherein the saponin is derived from a botanical source.

3. The composition of claim 2, wherein the botanical source is a plant of a Family Sapindaceae.

4. The composition of claim 2, wherein the botanical source is a plant of a genus Sapindus.

5. The composition of claim 1, wherein the saponin is derived from a source selected from Sapindus mukorossi and Sapindus trifoliatus.

6. The composition of claim 1, further comprising a surfactant selected from lecithin, pea protein, soy protein isolate, soy protein hydrolysate, alkyl polyglycosides, amino acid based-surfactants, glycolipid biosurfactants, and alkyl glucosides.

7. The composition of claim 1, wherein the solvent is selected from water, plant or flower water, and hydrosols.

8. The composition of claim 1, wherein the solvent is a water miscible humectant solvent.

9. The composition of claim 1, wherein the solvent comprises glycerin.

10. The composition of claim 1, having a pH of about 2 to about 7.

11. The composition of claim 1, further comprising Saccharomyces ferment.

12. The composition of claim 1 further comprising a component selected from shikimic acid and zinc ricinoleate.

13. The composition of claim 1, further comprising extract of aloe vera.

14. The composition of claim 1, further comprising a preservative.

15. The composition of claim 1, wherein the composition is substantially free of preservatives.

16. The composition of claim 1, further comprising an extract or oil selected from turmeric, ginger, seaweed, red and brown algae, neem, sandalwood, citronella, lemon eucalyptus, mineral extracts and mixtures thereof.

17. The composition of claim 1, wherein the solvent is a hydrosol selected from hydrosols of neem, calendula, witch hazel, chamomile, *Echinacea*, vetiver, tea tree, eucalyptus, lavender, *Rosmarinus officinalis*, rose geranium, oregano, summer savory, anise, cumin, balsam fir, cederwood, black thyme, *Bowellia carterii*, neroli, and *Mentha piperita* and mixtures thereof.

18. A textile impregnated with the composition of claim 1.

19. The textile of claim 18, wherein the textile is a non-woven matrix.

20. The textile of claim 18, wherein the textile is a woven matrix.

21. The textile of claim 18, wherein the textile is biodegradable.

22. The textile of claim 18, wherein the textile comprises a synthetic fiber.

23. The textile of claim 22, wherein the fiber is selected from rayon, acetate, polyester, aramid, acrylic, ingeo, olefin, regenerated cellulose, and polylactid.

24. The textile of claim 18, wherein the textile comprises a natural fiber.

25. The textile of claim 24, wherein the fiber is selected from bamboo, lotus stem, cotton, banana pseudo stem, pineapple leaves, pineapple stem, deciduous wood, palm, abaca, coir, jute, flax, kapok, kenaf, hemp, modal, ramie, sisal, soy protein and combinations thereof.

26. The cleansing and deodorizing composition of claim 1, for use in the treatment of a fungal infection of the skin.

27. The cleansing and deodorizing composition of claim 1, for use in the treatment of dandruff.

28. The composition of claim 1, wherein the surface is cleansed of a compound selected from naphthalene, acenaphthylene, acenaphthene, fluorene, phenanthrene, anthracene, fluoranthene, pyrene, benz[a]anthracene, chrysene, benzo[b]fluoranthene, benzo[k]fluoranthene, benzo[a]pyrene, dibenz[a,h]anthracene, benzo[ghi]perylene, indeno[1,2,3-cd]pyrene, benzo[c]fluorine, cyclopenta [cd]pyrene, dibenzo [a,e]pyrene, dibenzo [a,h]pyrene, dibenzo [a,i]pyrene, dibenzo [a,l]pyrene, 5-methyl chrysene, ozone, nitrous oxide, and an oxide of sulfur.

29. The composition of claim 1, wherein the saponin is present in the amount of about 1% to about 20%.

30. The composition of claim 29, wherein the cyclodextrin is present in the amount of about 1% to about 9%.

31. The composition of claim 1, wherein the cyclodextrin is present in the amount of 0.5% to about 2%.

* * * * *